(12) United States Patent
Duvvuru Muni et al.

(10) Patent No.: US 11,887,698 B2
(45) Date of Patent: Jan. 30, 2024

(54) METHOD AND ELECTRONIC DEVICE FOR BUILDING COMPREHENSIVE GENOME SCALE METABOLIC MODEL

(71) Applicant: Samsung Electronics Co., Ltd., Suwon-si (KR)

(72) Inventors: Rajasekhara Reddy Duvvuru Muni, Bangalore (IN); Tadi Venkata Siva Kumar, Bangalore (IN); Taeyong Kim, Daejeon (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 752 days.

(21) Appl. No.: 17/037,037

(22) Filed: Sep. 29, 2020

(65) Prior Publication Data

US 2021/0209100 A1 Jul. 8, 2021

(30) Foreign Application Priority Data

Jan. 8, 2020 (IN) .............................. 202041000851
Apr. 3, 2020 (KR) ........................ 10-2020-0041066

(51) Int. Cl.
*G01N 27/62* (2021.01)
*G16B 50/10* (2019.01)
(Continued)

(52) U.S. Cl.
CPC ............... *G16B 50/10* (2019.02); *G06F 7/08* (2013.01); *G06N 7/02* (2013.01); *G06N 20/00* (2019.01); *G16B 30/10* (2019.02); *G16B 40/00* (2019.02)

(58) Field of Classification Search
CPC ........ G16B 50/10; G16B 30/10; G16B 40/00; G06F 7/08; G06N 7/02; G06N 20/00; G06N 20/10
See application file for complete search history.

(56) References Cited

U.S. PATENT DOCUMENTS 6,291,182 B1   9/2001  Schork et al.
6,506,581 B1   1/2003  Fleischmann et al.
(Continued)

FOREIGN PATENT DOCUMENTS

JP   2007531874 A  *  3/2005  ............. G16B 30/00
KR   102314219 B1  * 10/2018  ............. G16B 20/00
(Continued)

OTHER PUBLICATIONS

Benedict, MN, "Likelihood-Based Gene Annotations for Gap Filling and Quality Assessment in Genome-Scale Metabolic Models," PLOS Computational Biology, Oct. 2014, vol. 10, Issue 10, www.plosconpbiol.org.

(Continued)

*Primary Examiner* — Hassan Mrabi
(74) *Attorney, Agent, or Firm* — CANTOR COLBURN LLP

(57) ABSTRACT

Systems and methods for building a comprehensive genome scale metabolic model. The method includes determining that at least one of a hypothetical profile annotation and an uncharacterized profile annotation is available in a profile annotation associated with a protein. Further, the method includes performing a machine learning procedure on at least one of the hypothetical profile annotation and the uncharacterized hypothetical profile annotation after a fuzzy string matching and ranking procedure. Further, the method includes obtaining all the possible protein annotations based on a fuzzy string matching procedure. Further, the method includes performing a rank procedure on at least one of the hypothetical profile annotation and the uncharacterized profile alternative annotation. Further, the method includes identifying all possible metabolic reactions for the protein annotation obtained by the fuzzy string matching procedure.

(Continued)

Further, the method includes ranking the protein annotation based on the metabolic reactions.

16 Claims, 6 Drawing Sheets

(51) Int. Cl.
*G06F 7/08* (2006.01)
*G06N 7/02* (2006.01)
*G06N 20/00* (2019.01)
*G16B 30/10* (2019.01)
*G16B 40/00* (2019.01)

(56) References Cited

U.S. PATENT DOCUMENTS

| | | | |
|---|---|---|---|
| 6,631,332 B2 | 10/2003 | Skolnick et al. | |
| 6,772,069 B1* | 8/2004 | Eisenberg | G16B 30/10 |
| | | | 435/7.1 |
| 7,925,484 B2* | 4/2011 | Dawson | G16B 15/00 |
| | | | 703/11 |
| 2003/0032066 A1* | 2/2003 | Legrain | G16B 20/00 |
| | | | 701/19 |
| 2004/0029149 A1 | 2/2004 | Palsson et al. | |
| 2014/0172318 A1 | 6/2014 | Fisher et al. | |
| 2015/0006090 A1 | 1/2015 | Pantaleoni | |
| 2016/0259880 A1 | 9/2016 | Semenyuk | |

FOREIGN PATENT DOCUMENTS

| | | | | |
|---|---|---|---|---|
| KR | 10-2018- 0128996 A | 12/2018 | | |
| WO | 2000-011206 A1 | 3/2000 | | |
| WO | WO-2016018481 A2 * | 2/2016 | ............... | C12Q 1/68 |
| WO | 2017-218908 A2 | 12/2017 | | |

OTHER PUBLICATIONS

Brettin, T., "RASTtk: A modular and extensible implementation of the RAST algorithm for building custom annotation pipelines and annotating batches of genomes," Scientific Reports, 5: 8365, DOI: 10.1038/srep08365.

Brendan King et al., 2018: ProbAnnoWeb and ProbAnnoPy: probabilistic annotation and gap-filling of metabolic reconstructions. Bioinformatics 34(9):1594-1596.

Ross Overbeek et al., 2014: The SEED and the Rapid Annotation of microbial genomes using Subsystems Technology (RAST). Nucleic Acids Research 42(D1):D206-D214.

* cited by examiner

METHOD AND ELECTRONIC DEVICE FOR BUILDING COMPREHENSIVE GENOME SCALE METABOLIC MODEL

CROSS REFERENCE TO RELATED APPLICATION

This application claims the benefit of and priority to Indian Patent Application 202041000851 as filed on Jan. 8, 2020, and Korea Patent Application No. 10-2020-0041066 as filed on Apr. 3, 2020, the disclosures of which are incorporated by reference herein in their entireties.

BACKGROUND

1. Field

The present disclosure relates to metabolic engineering, and more specifically to a method and electronic device for building a comprehensive Genome Scale Metabolic Model (GSMM).

2. Description of the Related Art

A GSMM enables exploring metabolic potential and engineering genomes. Construction of the GSMM involves identification of all reactions that are present in a genome. Once the reactions are identified, to enable the growth of an organism, additional reactions must be added using gap filling methodologies. Gap filling is a computational technique for adding reactions to GSMM to permit those models to run correctly. The gap filling technique completes what are incomplete models that lack fully connected metabolic networks. The gap filling methodologies often add spurious reactions.

Automated reaction identification systems based on partial genome annotation are incomplete. Gap filling on an incomplete reaction set often adds spurious reactions into the GSMM. In an example, approximately greater than 70% of identified proteins are annotated as hypothetical proteins in microbes. The metabolic reactions deduced from incompletely annotated genome are incomplete. The gap filling on the incomplete set of reactions yields additional unwanted/spurious reactions to the GSMM and affects the quality of GSMM analysis.

The GSMM is a powerful approach that allows for computationally simulating a variety of metabolic phenotypes. However, manually constructing accurate metabolic networks is extremely time intensive and it is thus desirable to have automated computational methods for providing high-quality metabolic networks. Incomplete knowledge of biological chemistries leads to missing, ambiguous, or inaccurate gene annotations, and thus gives rise to incomplete metabolic networks. Computational programs for filling these gaps in a metabolic model rely on network topology-based approaches that can result in solutions that are inconsistent with existing genomic data. In existing methods, the method can be used to directly incorporate genomic evidence into the decision-making process for gap filling reactions. The method can be used both for maximizing the consistency of gap filled reactions with available genomic data and identifying candidate genes for gap filled reactions. The method has been integrated into metabolic modeling services such as KBase or automated metabolic network reconstruction frameworks that includes the automated metabolic reconstruction tools such as ModelSEED.

Likelihood based gap filling such as ProbAnnoPy uses probabilistic annotation to compute organism-specific reaction likelihoods of gene functions based on sequence homology. However, the method will not take into account the diversity in genomes under investigation including gene gains and losses occurring due to horizontal gene transfer and gene duplications. Reaction identification is based on an enzymatic reaction's functional role. The functional role based reaction identification will effectively fill gaps but adds several unwanted and spurious reactions.

In other existing methods, the Rapid Annotation using Subsystem Technology (RAST) annotation engine annotates bacterial and archaeal genomes. The annotation engine is operated by offering a standard software pipeline for identifying genomic features (i.e., protein-encoding genes and RNA) and annotating their functions. Recently, in order to make RAST a more useful research tool and to keep pace with advancements in bioinformatics, it has become desirable to build a version of RAST that is both customizable and extensible; a modular version of RAST that enables researchers to build custom annotation pipelines. The RAST offers a choice of software for identifying and annotating genomic features as well as the ability to add custom features to an annotation job. The RAST also accommodates the batch submission of genomes and the ability to customize annotation protocols for batch submissions.

RAST system uses a K-mer similarity search only to find annotations. The RAST also picks annotations from related genomes. This step may cause wrong annotations in genome annotations because gene loss and gene gains across microbes is very common and such gene's portability will give erroneous reaction identification.

Thus, it is desired to address the above mentioned disadvantages or other shortcomings or at least provide a useful alternative.

SUMMARY

Embodiments herein provide a method and electronic device for building a comprehensive genome scale metabolic model.

Embodiments herein obtain a profile annotation associated with a protein from an annotation database.

Embodiments herein determine that at least one of a hypothetical profile annotation and an uncharacterized profile alternative annotation is available in the profile annotation associated with the protein.

Embodiments herein obtain all the possible protein annotations based on a fuzzy string matching procedure.

Embodiments herein perform a rank procedure on at least one of the hypothetical profile annotation and the uncharacterized profile alternative annotation.

Embodiments herein identify all possible metabolic reaction for the protein annotation obtained by the fuzzy string matching procedure.

Embodiments herein perform a machine learning procedure on at least one of the hypothetical profile annotation and the uncharacterized hypothetical profile alternative annotation after the fuzzy string matching and ranking procedure.

Embodiments herein i rank the protein annotation based on the metabolic reaction.

Embodiments herein perform a gap filling and flux balance analysis (FBA) on the ranked reaction annotation.

Additional aspects will be set forth in part in the description which follows and, in part, will be apparent from the description, or may be learned by practice of the presented embodiments of the disclosure.

Accordingly, embodiments herein disclose a method for building a comprehensive genome scale metabolic model. The method includes obtaining, by an electronic device, a profile annotation associated with a protein from an annotation database. Further, the method includes determining, by the electronic device, that at least one of a hypothetical profile annotation and an uncharacterized profile alternative annotation is available in the obtained profile annotation associated with the protein. Further, the method includes obtaining, by the electronic device, all the possible protein annotations from the obtained profile annotation based on a fuzzy string matching procedure. Further, the method includes performing, by the electronic device, a rank procedure on at least one of the hypothetical profile annotation and the uncharacterized profile alternative annotation based on the obtained all the possible protein annotations. Further, the method includes identifying, by the electronic device, all possible metabolic reaction for the protein annotation obtained by the fuzzy string matching procedure using the rank procedure. Further, the method includes ranking, by the electronic device, the protein annotation based on the identified all possible metabolic reaction.

In an embodiment, obtaining, by the electronic device, all possible protein annotations includes performing a machine learning procedure on at least one of the hypothetical profile annotation and the uncharacterized hypothetical profile alternative annotation after the fuzzy string matching procedure and the ranking procedure, and obtaining the protein annotation based on the fuzzy string rank procedure and the machine learning procedure.

In an embodiment, the annotation database comprises a compilation of sequences with a maximum annotation diversity and minimum sequence redundancy.

In an embodiment, the protein annotation is ranked based on at least one of an alignment length of the protein, mismatches of the alignment length of the protein, gap length of the protein, and a sequence length of the protein.

In an embodiment, the metabolic reaction is identified based on a complex identified in the protein annotation and a unique occurrence in the protein annotation.

In an embodiment, the method further includes performing a gap filling and flux balance analysis on the ranked protein annotation. Further, the method further includes generating a comprehensive GSMM model based on the gap filling and flux balance analysis.

In an embodiment, the ranked protein annotation is used to mine the metabolic reaction using the fuzzy string matching procedure.

In an embodiment, the profile annotation is a sequence similarity based profile annotation, reaction identification compliant profile annotation, and a non-sequence similarity based profile annotation.

Accordingly, embodiments herein disclose an electronic device for building a comprehensive genome scale metabolic model. The electronic device includes a processor coupled with a memory. The processor is configured to obtain a profile annotation associated with a protein from an annotation database. Further, the processor is configured to determine that at least one of a hypothetical profile annotation and an uncharacterized profile uncharacterized profile annotation is available in the obtained profile annotation associated with the protein. Further, the processor is configured to obtain all the possible protein annotations from the obtained profile annotation based on the fuzzy string matching procedure. Further, the processor is configured to perform a rank procedure on at least one of the hypothetical profile annotation and the uncharacterized profile alternative annotation based on the obtained all the possible protein annotations. Further, the processor is configured to identify all possible metabolic reaction for the protein annotation by fuzzy string matching using the rank procedure. Further, the processor is configured to rank the protein annotation based on the identified all possible metabolic reaction.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The above and other aspects, features, and advantages of certain embodiments of the disclosure will be more apparent from the following description taken in conjunction with the accompanying drawings, in which.

This method is illustrated in the accompanying drawings, throughout which like reference letters indicate corresponding parts in the various figures. The embodiments herein will be better understood from the following description with reference to the drawings, in which.

DETAILED DESCRIPTION

Figure 1:
FIG. 1 illustrates a process for building a comprehensive genome scale metabolic model.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

As is traditional in the field, embodiments may be described and illustrated in terms of blocks which carry out a described function or functions. These blocks, which may be referred to herein as units or modules or the like, are physically implemented by analog or digital circuits such as logic gates, integrated circuits, microprocessors, microcontrollers, memory circuits, passive electronic components, active electronic components, optical components, hardwired circuits, or the like, and may optionally be driven by firmware and software. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks without departing from the scope of the invention. Likewise, the blocks of the embodiments may be physically combined into more complex blocks without departing from the scope of the invention The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings. Although the terms first, second, etc. may be used herein to describe various elements, these elements should not be limited by these terms. These terms are generally only used to distinguish one element from another.

Accordingly, embodiments herein achieve a method for building a comprehensive genome scale metabolic model. The method includes obtaining, by an electronic device, a profile annotation associated with a protein from an annotation database. Further, the method includes determining, by the electronic device, that at least one of a hypothetical profile annotation and an uncharacterized profile alternative annotation is available in the obtained profile annotation associated with the protein. Further, the method includes obtaining, by the electronic device, all the possible protein annotations from the obtained profile annotation based on a fuzzy string matching procedure. Further, the method includes performing, by the electronic device, a rank procedure on at least one of the hypothetical profile annotation and the uncharacterized profile alternative annotation based on the obtained all the possible protein annotations. Further, the method includes identifying, by the electronic device, all possible metabolic reaction for the protein annotation obtained by the fuzzy string matching procedure using the using the rank procedure. Further, the method includes ranking, by the electronic device, the protein annotation based on the identified all possible metabolic reaction.

Unlike conventional methods and system, the methods disclosed herein can be used to maximize the number of genome annotations that can be identified from a genome using a fuzzy string matching procedure. The fuzzy string matching procedure is a technique of finding strings that match a pattern approximately (rather than exactly). Once annotations are identified, the method can be used to rank each annotation as per alignment parameters. These ranked annotations are used to mine metabolic reactions and are ranked by uniqueness of the reaction and complex identified. This significantly improves the number of reactions identified from the genome and reduces gap filling reactions added.

The disclosed methods can be used to automatically construct the genome scale metabolic model from a genome sequence. In the disclosed methods, an integrated sequence homology and a machine learning genome annotation methodology can annotate highest number of proteins in the genome under investigation. The fuzzy string matching procedure based reaction identification from ranked annotations leads to reduced gap filling reactions and enables the comprehensive genome scale metabolic model in an accurate manner. The higher number of genome specific reactions identified leads to high quality genome scale metabolic models. The deep and high quality genome scale metabolic models enable industrial biotechnologists to explore opportunities in synthetic biology, metabolic engineering and strain design across biopharma, bioremediation, bio production of high value compounds.

The methods can be used to maximize genome specific reactions based on specific genome annotation, provide feasible metabolic reactions from the deduced annotations, and reduce hypothetical, un-annotated proteins during genome annotation.

The methods can be used to identify the reactions mapped to ranked annotations of proteins based on fuzzy string matching procedure. Based on the disclosed methods, a large portion of a microbial genome gets annotated. The methods can be used to identify the reactions from a given genome.

In the disclosed methods, the genome annotation may be performed using a custom annotation database with maximum annotation diversity and minimum sequence redundancy. The methods can be used to enhance the identification of reactions from the annotated enzymes. The methods can be used to annotate genomes for accurate annotation of proteins and subsequent metabolic reaction identification enabling genome scale metabolic model construction.

Referring now to the drawings, and more particularly to FIGS. 2 through 6, there are shown various embodiments.

Figure 2:
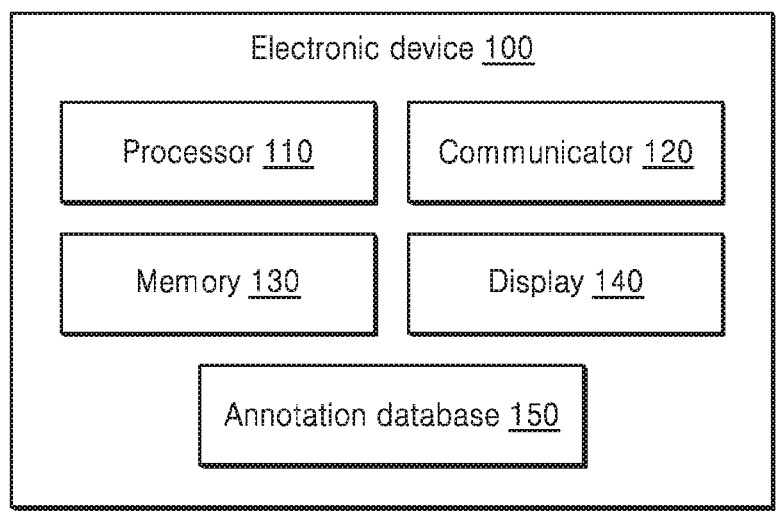
FIG. 2 illustrates various hardware components of an electronic device for building a comprehensive genome scale metabolic model, according to an embodiment as disclosed herein.

FIG. 2 illustrates various hardware components of an electronic device (100) for building a comprehensive genome scale metabolic model, according to an embodiment as disclosed herein. The electronic device (100) can be, for example, but not limited to a cellular phone, a smart phone, a Personal Digital Assistant (PDA), a tablet computer, a laptop computer, a desktop computer, a supercomputer, a smart watch, an Internet of Things (IoT) or the like.

In an embodiment, the electronic device (100) includes a processor (110), a communicator (120), a memory (130), a display (140) and an annotation database (150). The processor (110) is coupled with the communicator (120), the memory (130), the display (140) and the annotation database (150).

In an embodiment, the processor (110) is configured to obtain a profile annotation associated with a protein from the annotation database (150). The profile annotation can be, for example, but not limited to a HMMER profile annotation, a BLAST profile annotation or the like. The profile annotation can be used to identify homologous protein or nucleotide sequences, and to perform sequence alignments.

In an embodiment, the profile annotation may be a sequence similarity based profile annotation, reaction identification compliant profile annotation, or a non-sequence similarity based profile annotation.

In an embodiment, the annotation database (150) includes a compilation of sequences with a maximum annotation diversity and minimum sequence redundancy. The annotation database (150) is provided with maximum annotation diversity and minimum sequence redundancy. Table 1 indicates a knowledgebase creation and assessment.

TABLE 1

| Annotation database | Number of sequence | Curated database |
|---|---|---|
| Uniprot (EC numbered proteins from kingdome bacteria) | 194,191 | 155,418 |
| Metacyc protein sequences | 10,630 | 10,630 |
| SEED database | 32,415,017 | 15,974,003 |
| Total | 32,619,838 | 16,140,051 |

Further, the processor (110) is configured to determine that at least one of a hypothetical profile annotation and an uncharacterized profile annotation is available in the profile annotation associated with the protein. Further, the processor (110) is configured to obtain all the possible protein annotations using a fuzzy string matching procedure or other matching procedure. Further, the processor (110) is configured to perform a rank procedure on the at least one of the hypothetical profile annotation and the uncharacterized profile alternative annotation. Further, the processor (110) is configured to identify all possible metabolic reactions for the protein annotation using a fuzzy string matching procedure. Further, the processor (110) is configured to rank the protein annotation based on the identified metabolic reactions.

In an embodiment, all the possible protein annotation is obtained by performing a machine learning procedure on the at least one of the hypothetical profile annotation and the uncharacterized hypothetical profile alternative annotation after performing the fuzzy string matching and the ranking procedure.

In an example, table 2 indicates the protein annotation based on sequence features using a machine learning procedure such as support vector machine (SVM), RF, Deep Learning or the like.

TABLE 2

| Contig | Prokka annotation | EC predicted | Quality score | Annotation for the EC |
|---|---|---|---|---|
| MC_contig_00043 | Hypothetical protein | 1.1.1.193 | 0.87 | 5-amino-6-(5-phosphoribosyl-amino)uracial reducatase (EC 1.1.1.1) |
| MC_contig_00043 | Hypothetical protein | 1.14.13.- | 0.78 | 2-OCTAPRENYL-3-METHYL-6-METHOXY-1,4-BENZOQUINOL HYDROXYLASE (EC 1.14.13.-) |
| MC_contig_00043 | Hypothetical protein | 1.14.13.- | 0.78 | VANILLATE ODEMETH-YLASE OXIDO-REDUCTASE (EC 1.14.13.-) |
| MC_contig_00043 | Hypothetical protein | 1.14.13.- | 0.78 | NITRILOTRI-ACETATE MONO-OXYGENASE COMPONENT A (EC 1.14.13.- ) |
| MC_contig_00043 | Hypothetical protein | 3.5.4.26 | 0.87 | Diaminohydroxy phosphoribosyl-aminopyrimidine deaminase (EC 3.5.4.26) |

In an embodiment, the protein annotation is ranked based on at least one of an alignment length of the protein, mismatches of the alignment length of the protein, a gap length of the protein, a sequence length of the protein or the like. The ranking for the protein annotation may be performed based on any of the Equations (1-3), for example.

$$f_{align} = \text{alignment length/sequence length} \quad (1)$$

$$f_{mismatch} = \text{mismatch+gaplength+evalue} \quad (2)$$

$$\text{Rank} = f_{align}/(f_{align}+f_{mismatch}) \quad (3)$$

Table 3 indicates a fuzzy string matching result.

TABLE 3

| Entry | Protein names | Match hit (200 400 600 800) | Identity |
|---|---|---|---|
| Q6DR24 | Uncharacterized protein At3g17950 (Arabidopsis thaliana) | — | 100% |
| D7L7Y2 | Uncharacterized protein (Arabidopsis lyrate subsp. lyrata) | — | 91.1% |
| R0G765 | Uncharacterized protein (Capsella rubella) | — | 89.7% |
| A0A119LLG8 | Transmembrane protein (Arabidopsis thaliana) | — | 100% |

In an embodiment, a metabolic reaction may be identified based on a complex identified in the protein annotation and a unique occurrence in the protein annotation.

In an example, ranked probable gene annotations are used to identify reactions from the modelSEED database using the fuzzy string matching procedure. The reactions identified are filtered and ranked based on a complex identified and a unique occurrence as shown in Table 4.

TABLE 4

| Prokka annotation | Feature based annotation | Complex identified | Reactions identified |
|---|---|---|---|
| MCC_contig_00043 hypothetical protein | 5-amino-6-(5-phos- phoribosylamino)uracil reductase (EC 1.1.1.193) | [cpx.1021 cpx.543, cpx.2459] | [rxn02474, rxn02475] |
| MCC_contig_00043 hypothetical protein | Diaminohydroxy- phosphoribosylamino pyrimidine deaminase (EC 3.5.4.26) | [cpx.1021, cpx.3143] | [rxn02475] |

In an embodiment, the processor (110) is configured to perform a gap filling and flux balance analysis on the ranked protein annotation. Further, the processor (110) is configured to generate the GSMM model based on the gap filling and flux balance analysis. In an embodiment, the ranked protein annotation is used to mine the metabolic reaction(s) using the fuzzy string matching procedure.

The processor (110) is configured to execute instructions stored in the memory (130) and to perform various processes. The communicator (120) includes circuitry or components configured for communicating internally between internal hardware components and with external devices via one or more networks. In an embodiment, the annotation database (150) is a part of the memory (130). In another embodiment, the annotation database (150) is stored external to the memory (130).

The memory (130) also stores instructions to be executed by the processor (110). The memory (130) may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the memory (130) may, in some examples, be considered a non-transitory storage medium. The term "non-transitory" may indicate that the storage medium is not embodied in a carrier wave or a propagated signal. However, the term "non-transitory" should not be interpreted that the memory (130) is non-movable. In some examples, the memory (130) can be configured to store larger amounts of information than the memory. In certain examples, a non-transitory storage medium may store data that can, over time, change (e.g., in Random Access Memory (RAM) or cache).

Although FIG. 2 shows various hardware components of the electronic device (100), it is to be understood that other embodiments are not limited thereon. In other embodiments, the electronic device (100) may include less or more number of components. Further, the labels or names of the components are used only for illustrative purpose and do not limit the scope of the invention. One or more components can be combined together to perform the same or substantially similar functions to build the comprehensive genome scale metabolic model.

Figure 3:
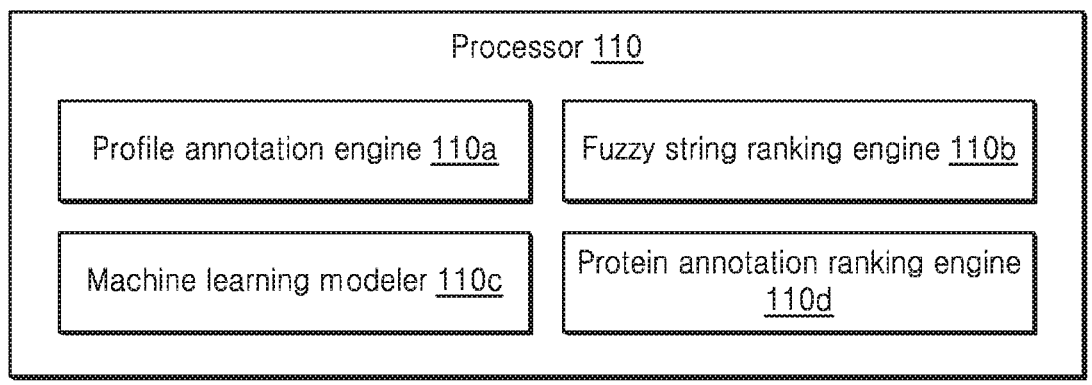
FIG. 3 illustrates various hardware components of a processor included in the electronic device, according to an embodiment as disclosed herein.

FIG. 3 shows various hardware components of the processor (110), according to an embodiment. In an embodiment, the processor (110) includes a profile annotation engine (110a), a fuzzy string ranking engine (110b), a machine learning modeler (110c) and a protein annotation ranking engine (110d). The profile annotation engine (110a) is configured to obtain the profile annotation associated with the protein from the annotation database (150). The fuzzy string ranking engine (110b) is configured to determine that at least one of the hypothetical profile annotation and the uncharacterized profile alternative annotation is available in the profile annotation associated with the protein.

The machine learning modeler (110c) is configured to perform the machine learning procedure on at least one of the hypothetical profile annotation and the uncharacterized hypothetical profile alternative annotation after the fuzzy string matching and ranking procedures. The protein annotation ranking engine (110d) is configured to obtain all the possible protein annotations based on the fuzzy string matching procedure and perform the rank procedure on at least one of the hypothetical profile annotation and the uncharacterized profile alternative annotation. Further, the protein annotation ranking engine (110d) is configured to identify all possible metabolic reactions for the protein annotation obtained by the fuzzy string matching procedure and the machine learning procedure. Further, the protein annotation ranking engine (110d) is configured to rank the protein annotation based on the metabolic reactions.

Although FIG. 3 shows various hardware components of the processor (110), it is to be understood that other embodiments are not limited thereon. In other embodiments, the processor (110) may include less or more number of components. Further, the labels or names of the components are used only for illustrative purpose and do not limit the scope of the invention. One or more components can be combined together to perform the same or substantially similar functions to build the comprehensive genome scale metabolic model.

Figure 4:
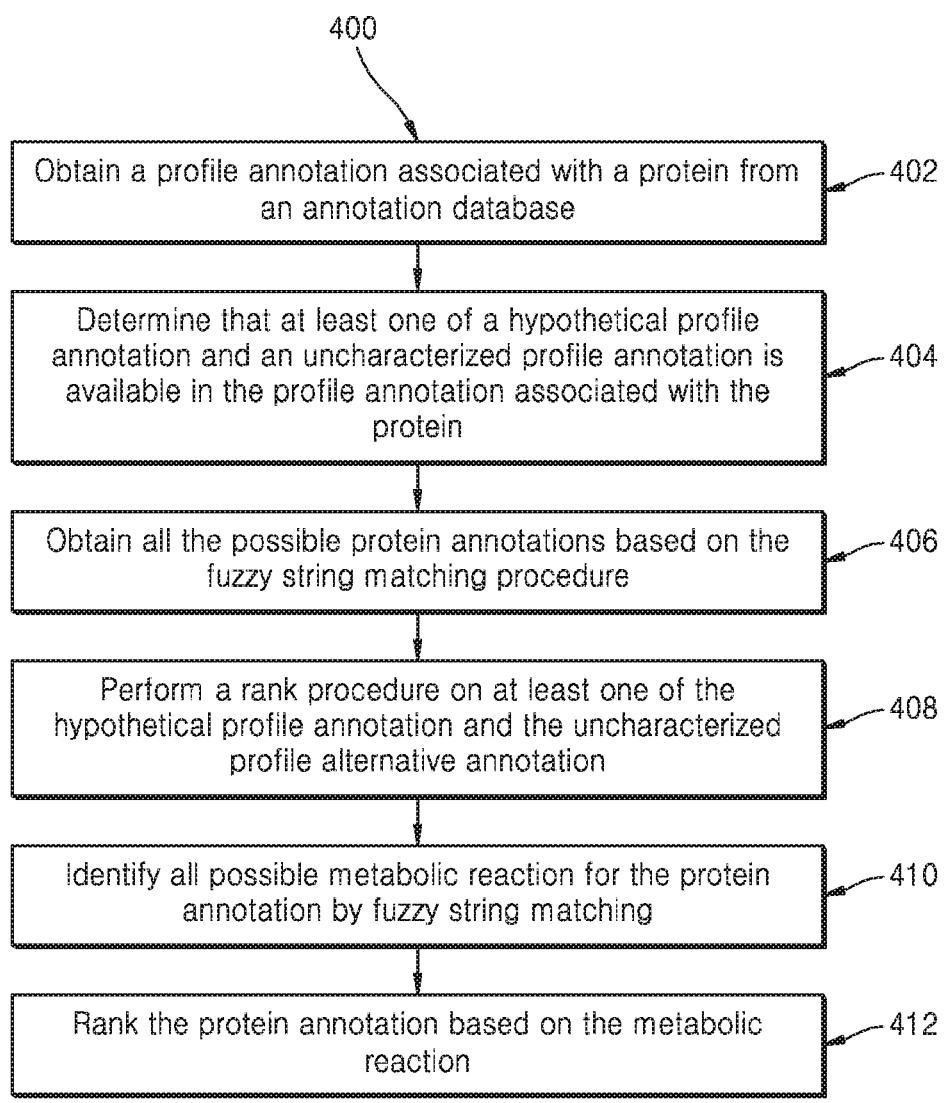
FIG. 4 is a flow chart illustrating a method for building the comprehensive genome scale metabolic model, according to an embodiment as disclosed herein.

FIG. 4 is a flow chart (400) illustrating a method for building the comprehensive genome scale metabolic model, according to an embodiment. The operations (402-412) are performed by the processor (110).

At 402, the method includes obtaining the profile annotation associated with the protein from the annotation database (150). At 404, the method includes determining that at least one of a hypothetical profile annotation and an uncharacterized profile alternative annotation is available in the profile annotation associated with the protein. At 406, the method includes obtaining all the possible protein annotations based on the fuzzy string matching procedure. At 408, the method includes performing the rank procedure on the at least one of the hypothetical profile annotation and the uncharacterized profile alternative annotation. At 410, the method includes identifying all possible metabolic reactions for the protein annotation using a fuzzy string matching procedure. At 412, the method includes ranking the protein annotation based on the metabolic reaction(s).

Figure 5:
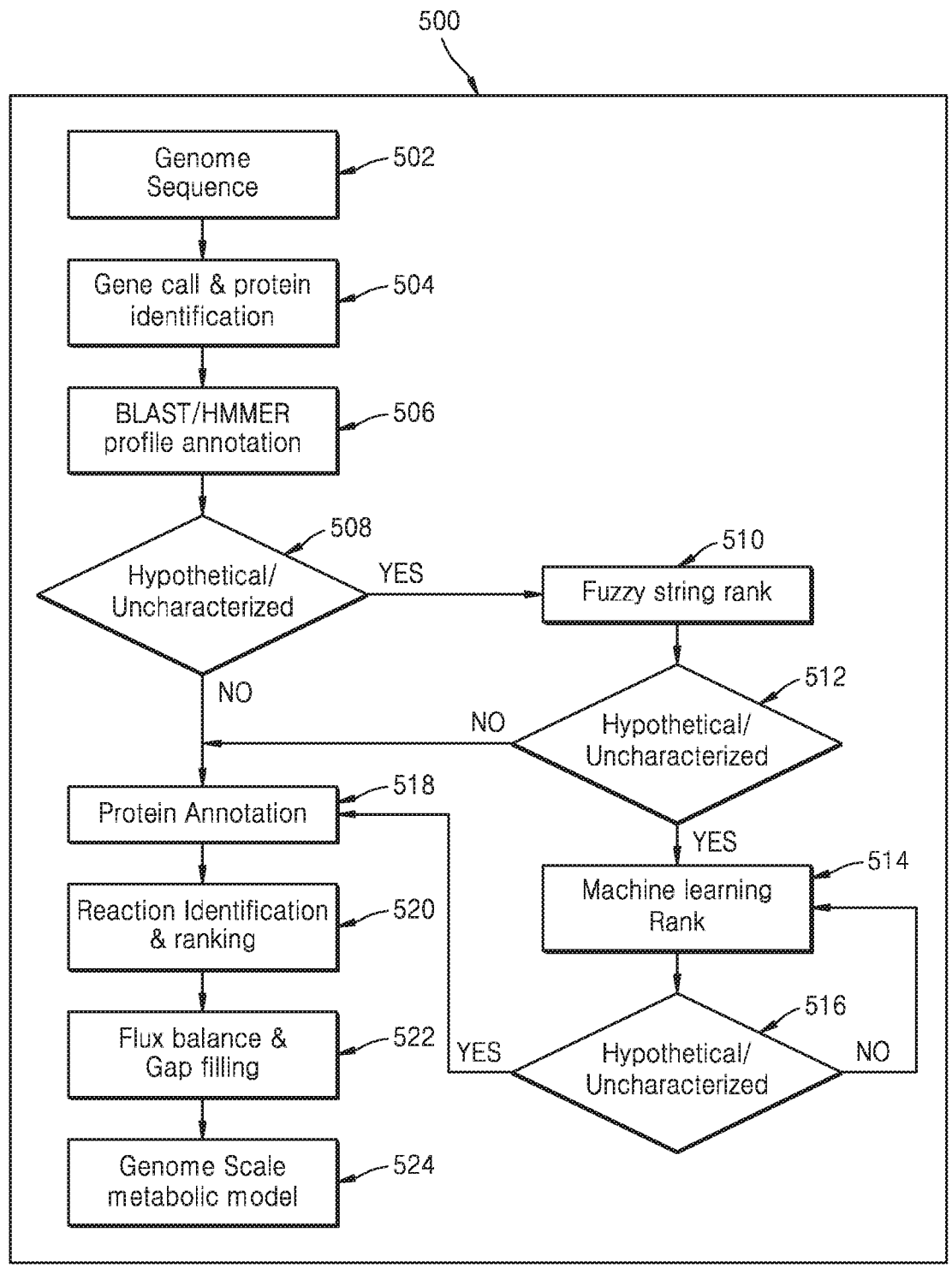
FIG. 5 is an example flow chart illustrating a method for building the comprehensive genome scale metabolic model, according to an embodiment as disclosed herein.

FIG. 5 is an example flow chart (500) illustrating a method for building the comprehensive genome scale metabolic model, according to an embodiment. The operations (502-524) are performed by the processor (110).

At 502, the method includes obtaining a genome sequence. At 502, the method includes identifying a protein from the genome sequence. At 506, the method includes obtaining a profile annotation (e.g., HMMER profile annotation, BLAST profile annotation or the like) associated with the protein from the annotation database (150). At 508, the method includes determining that at least one of a hypothetical profile annotation and an uncharacterized profile alternative annotation is available in the profile annotation associated with the protein.

If the at least one of the hypothetical profile annotation and the uncharacterized profile alternative annotation is available in the profile annotation associated with the protein then, at 510, the method includes obtaining all the possible protein annotations using fuzzy string matching procedure.

At 512, the method includes determining that at least one of the hypothetical profile annotation and the uncharacterized profile alternative annotation is available in the profile annotation associated with the protein after the fuzzy string matching procedure. If the at least one of the hypothetical profile annotation and the uncharacterized profile alternative annotation is available in the profile annotation associated with the protein then, at 514, the method includes performing a machine learning procedure on at least one of the hypothetical profile annotation and the uncharacterized hypothetical profile annotation after the fuzzy string matching and ranking procedures. At 516, the method includes determining that at least one of the hypothetical profile annotation and the uncharacterized profile alternative annotation is available in the profile annotation associated with the protein after the fuzzy string rank procedure and the machine learning procedure.

At 518, the method includes obtaining the protein annotation. At 520, the method includes performing a rank procedure on at least one of the hypothetical profile annotation and the uncharacterized profile alternative annotation. Further, the method includes identifying all possible metabolic reactions for the protein annotation. At 522, the method includes ranking the protein annotation based on the metabolic reactions. At 522, the method includes performing a gap filling and flux balance analysis on the ranked protein annotation. At 524, the method includes generating the GSMM model based on the gap filling and flux balance analysis.

Figure 6:
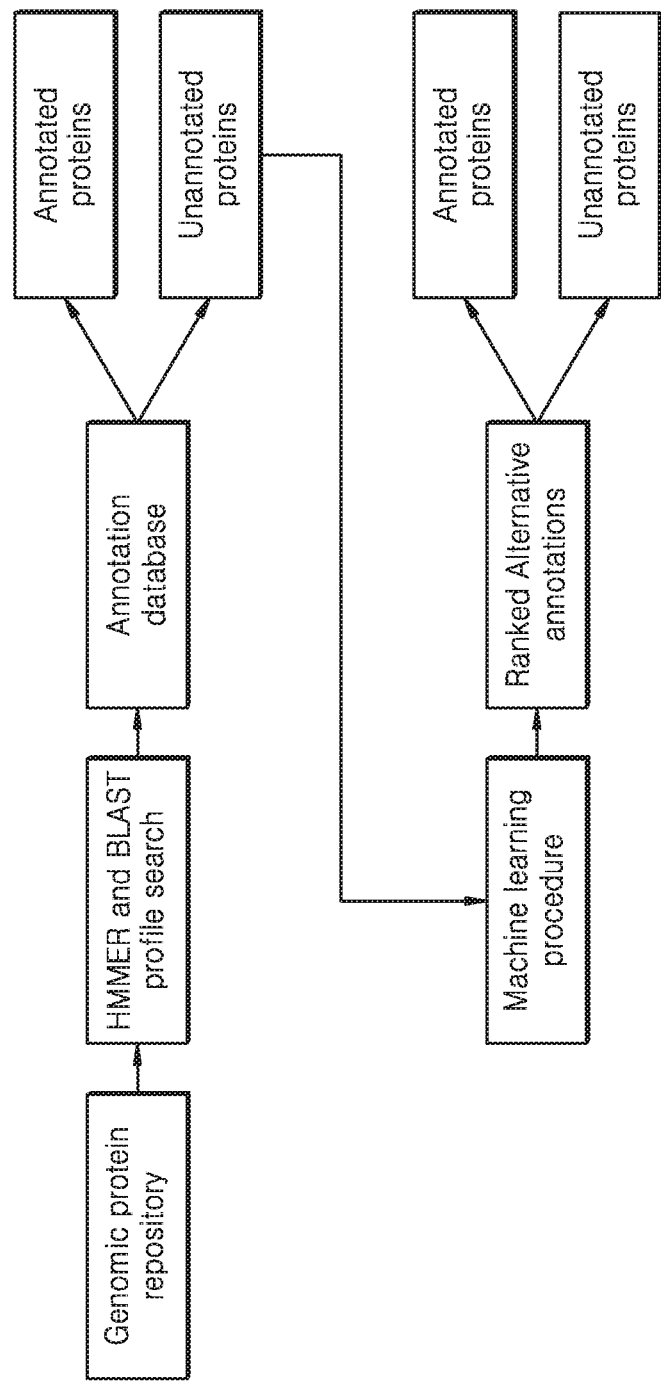
FIG. 6 is an another example process flow illustrating a method for building the comprehensive genome scale metabolic model, according to an embodiment as disclosed herein.

Another example process flow illustrating a method for building the comprehensive genome scale metabolic model is explained in the FIG. 6. The operations of the FIG. 6 is similar to the operations of the FIG. 5.

The various actions, acts, blocks, steps, or the like in the flow charts (400 and 500) may be performed in the order presented, in a different order or simultaneously. Further, in some embodiments, some of the actions, acts, blocks, steps, or the like may be omitted, added, modified, skipped, or the like without departing from the scope of the invention.

The embodiments disclosed herein can be implemented using at least one software program running on at least one hardware device and performing network management functions to control the elements.

The foregoing description of the specific embodiments will also reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

What is claimed is:

1. A method for building a comprehensive genome scale metabolic model, comprising:
   obtaining, by an electronic device, a profile annotation associated with a protein from an annotation database;
   determining, by the electronic device, that at least one of a hypothetical profile annotation and an uncharacterized profile alternative annotation is available in the obtained profile annotation associated with the protein;
   obtaining, by the electronic device, all possible protein annotations from the obtained profile annotation using a fuzzy string matching procedure;
   performing, by the electronic device, a rank procedure on at least one of the hypothetical profile annotation and the uncharacterized profile alternative annotation based on the obtained possible protein annotations;
   identifying, by the electronic device, all possible metabolic reactions for the protein annotation obtained by the fuzzy string matching procedure using the rank procedure; and
   ranking, by the electronic device, the protein annotation based on the identified possible metabolic reactions.

2. The method of claim 1, wherein obtaining, by the electronic device, all possible protein annotations comprise:
   performing, by the electronic device, a machine learning procedure on at least one of the hypothetical profile annotation and the uncharacterized hypothetical profile alternative annotation after the fuzzy string matching and ranking procedure; and
   obtaining, by the electronic device, the protein annotation based on a result of the fuzzy string rank procedure and the machine learning procedure.

3. The method of claim 1, wherein the annotation database comprises a compilation of sequences with a maximum annotation diversity and minimum sequence redundancy.

4. The method of claim 1, wherein the protein annotation is ranked based on at least one of an alignment length of the protein, mismatches of the alignment length of the protein, gap length of the protein, and a sequence length of the protein.

5. The method of claim 1, wherein the metabolic reaction is identified based on a complex identified in the protein annotation and a unique occurrence in the protein annotation.

6. The method of claim 1, further comprising:
   performing a gap filling and flux balance analysis on the ranked protein annotation; and
   generating the comprehensive Genome Scale Metabolic Model based on the gap filling and flux balance analysis.

7. The method of claim 1, wherein the ranked protein annotation is used to mine the metabolic reaction using the fuzzy string matching procedure.

8. The method of claim 1, wherein the profile annotation is a sequence similarity based profile annotation, reaction identification compliant profile annotation, and a non-sequence similarity based profile annotation.

9. An electronic device for building a comprehensive genome scale metabolic model, comprising:
   a memory;
   a processor, coupled with the memory, configured to:
   obtain a profile annotation associated with a protein from an annotation database;
   determine that at least one of a hypothetical profile annotation and an uncharacterized profile uncharacterized profile annotation is available in the obtained profile annotation associated with the protein;

obtain all the possible protein annotations from the obtained profile annotation using a fuzzy string matching procedure;

perform a rank procedure on at least one of the hypothetical profile annotation and the uncharacterized profile alternative annotation based on the obtained possible protein annotations;

identify all possible metabolic reactions for the protein annotation obtained by fuzzy string matching using the rank procedure; and rank the protein annotation based on the identified all possible metabolic reactions.

10. The electronic device of claim 9, wherein obtain all the possible protein annotation comprises:

perform a machine learning procedure on at least one of the hypothetical profile annotation and the uncharacterized hypothetical profile annotation after the fuzzy string matching and ranking procedure; and obtain a protein annotation based on the fuzzy string rank procedure and the machine learning procedure.

11. The electronic device of claim 9, wherein the annotation database comprises a compilation of sequences with a maximum annotation diversity and minimum sequence redundancy.

12. The electronic device of claim 9, wherein the protein annotation is ranked based on at least one of an alignment length of the protein, mismatches of the alignment length of the protein, gap length of the protein, and a sequence length of the protein.

13. The electronic device of claim 9, wherein the metabolic reaction is identified based on a complex identified in the protein annotation and a unique occurrence in the protein annotation.

14. The electronic device of claim 9, wherein the processor is configured to:

perform a gap filling and flux balance analysis on the ranked protein annotation; and generate a Genome Scale Metabolic Model (GSMM) based on the gap filling and flux balance analysis.

15. The electronic device of claim 9, wherein the ranked protein annotation is used to mine the metabolic reaction using the fuzzy string matching procedure.

16. The electronic device of claim 9, wherein the profile annotation is a sequence similarity based profile annotation, reaction identification compliant profile annotation, and a non-sequence similarity based profile annotation.

* * * * *